United States Patent [19]

Ando et al.

[11] 4,430,432
[45] Feb. 7, 1984

[54] ENDO-DEOXYRIBONUCLEASE AND PROCESS FOR THE PRODUCTION THEREOF

[75] Inventors: Tadahiko Ando; Takehiko Shibata; Hiroomi Watabe, all of Tokyo, Japan

[73] Assignee: Rikagaku Kenkyusho, Wako, Japan

[21] Appl. No.: 353,226

[22] Filed: Mar. 1, 1982

[30] Foreign Application Priority Data

Mar. 9, 1981 [JP] Japan ................... 56-33321

[51] Int. Cl.³ .................. C12N 9/22; C12N 15/00; C12R 1/84; C12R 1/85
[52] U.S. Cl. ..................... 435/199; 435/172; 435/938; 435/940
[58] Field of Search ......................... 435/199

[56] References Cited

PUBLICATIONS

Bethesda Research Laboratories (BRL) 1981 Reference Chart–Restriction Endonuclease Reference Chart.

Primary Examiner—Lionel M. Shapiro
Attorney, Agent, or Firm—Bucknam and Archer

[57] ABSTRACT

A novel Endo-deoxyribonuclease A (Endo-DNase A) which has the substrate specificity of recognizing specific base sequence in double-stranded deoxyribonucleic acid (DNA) molecules and cleaving the strands at specified sites in the DNA to produce specific DNA fragments and, a process for the production of the Endo-DNase A by culturing a microorganism belonging to the genus Saccharomyces or Pichia.

5 Claims, 4 Drawing Figures

ENDO-DEOXYRIBONUCLEASE AND PROCESS FOR THE PRODUCTION THEREOF

BACKGROUND OF THE INVENTION

1. Field of the Invention

This invention relates to a novel Endo-deoxyribonuclease (hereinafter referred to as "Endo-DNase") and a process for the production thereof and more particularly, a novel Endo-deoxyribonuclease A (hereinafter referred to as "the Endo-DNase A" or "the DNase A") which has the substrate specificity of recognizing specific base sequence in double-stranded deoxyribonucleic acid (DNA) molecules and cleaving the strands at specified sites in the DNA to produce specific DNA fragments and, a process for the production of the Endo-DNase A which comprises culturing an Endo-DNase A-producing microorganism belonging to the genus Saccharomyces or Pichia and treating the resulting cell-free extract to separate and collect the Endo-DNase A.

The term "novel Endo-deoxyribonuclease A (Endo-DNase A)" means an enzyme according to the present invention and has physico-chemical properties and a substrate specificity which are explained hereinafter.

Deoxyribonuclease (DNase) which degrades deoxyribonucleic acid (DNA) exists in various biological materials, and is involved the important processes of vital functions including DNA metabolism, such as degradation, synthesis and genetic recombination of DNA and public attention has recently been paid to its enzymatic chemical properties and biochemical functions. On the other hand, it has become of great importance that an enzyme having specific functions be produced and separated in order to study the structure and function of gene DNA and to use the enzyme as a biochemical reagent, especially means for gene cloning, for the purpose of breeding.

2. Description of the Prior Art

DNases are generally classified into exonucleases and endonucleases according to their mode of action. The former type acts on the terminal of polynucleotide chain of DNA molecule and hydrolyzes the chain progressively to liberate nucleotides, while the latter cleaves phosphodiester bond in DNA molecule distributively to produce DNA fragments or oligonucleotides. Recently, in the field of endonuclease type enzymes, many studies have been carried out with respect to enzymes having a specificity to the structure of DNA, particularly to the nucleotide sequence or the structural change which exists in nature or is artificially introduced, enzymes recognizing and acting on DNA of a specific organism, or enzymes having biologically important functions (see Tadahiko Ando, Chemistry and Life, Vol. 13, No. 6, p. 342, (1975)).

The inventors of the present invention have performed a series of studies with respect to processes for the production of enzymes and have established some processes which are: a process for producing an enzyme which preferentially cleaves purine-purine linkage in DNA molecule from the cell of *Aspergillus oryzae* (Japanese Pat. No. 621,205); a process for production an enzyme which preferentially cleaves guanine-guanine linkage in DNA molecule from the culture liquid of alkalophilic bacteria (Japanese Pat. No. 831,171); and, a process for producing three Endo-DNases which recognize the DNA of a specific organism and cleave specific sites in the DNA molecule to form DNA fragments of specific size from the cells of *Sporogenous aerobic* belonging to the genus Bacillus (Japanese Pat. No. 1,008,416).

Studies of DNase which recognizes the feature of the primary (nucleotide sequence) or high order structure of DNA and acts on the DNA, have recently been directed to clarification of functions of DNA in important processes in cells such as DNA replication, genetic recombination, DNA repair or restriction and modification, and to research and use of enzymes which may be utilized to analysis of DNA structure, formation of site-specific mutagenesis, process for genetic recombination of DNA in vitro, and the like.

Some site-specific endonuclease which recognize specified base sequences in DNA molecules and cleave the strands at specified sites within or near the sequence to produce specific DNA fragments, that is, the restriction enzyme (II) which concerns restriction and modification in procaryotes, and the other various enzymes having similar functions to the enzyme (II) have been found and many of them have been isolated (see Tadahiko Ando, "Restriction enzyme", Chemistry and Life, Vol. 17, No. 5, p. 311, (1979); Tadahiko Ando, "What is a restriction enzyme?—Specificity of restriction enzyme and use thereof", Chemistry, Vol. 35, No. 1, p. 20, (1980)).

However, no enzymes of the type described above have ever been discovered in eucaryotes. The inventors of the present invention conducted the study of a new DNase having the specific function described above with respect to various yeasts belonging to eucaryotes and have succeeded in separating and collecting a novel DNase A which has the substrate specificity of recognizing the base sequence in double-stranded DNA molecules and cleaving the strands at specific sites in the DNA to produce specific DNA fragments, from the cell-free extract obtained by culturing Saccharomycetaceae such as *Saccharomyces uvarum* or *Saccharomyces cerevisiae* which belongs to the genus Saccharomyces, and *Pichia membranaefaciens* which belongs to the genus Pichia. The inventors established the process for production of the DNase A and completed the present invention.

SUMMARY OF THE INVENTION

This invention relates to a novel Endo-deoxyribonuclease A which has the substrate specificity of recognizing specific base sequence in double-stranded deoxyribonucleic acid (DNA) molecules and cleaving the strands at specific sites in the DNA to produce specific DNA fragments and, a process for the production of the DNase A by culturing a DNase A-producing microorganism belonging to the genus Saccharomyces or Pichia and treating the resulting cell-free extract to separate and collect the DNase A.

The Endo-DNase A according to the present invention, as described above, may widely be used as a biochemical reagent to study the structure and function of gene DNA and employed to gene cloning for breeding.

DETAILED DESCRIPTION OF THE INVENTION

Figure 1:
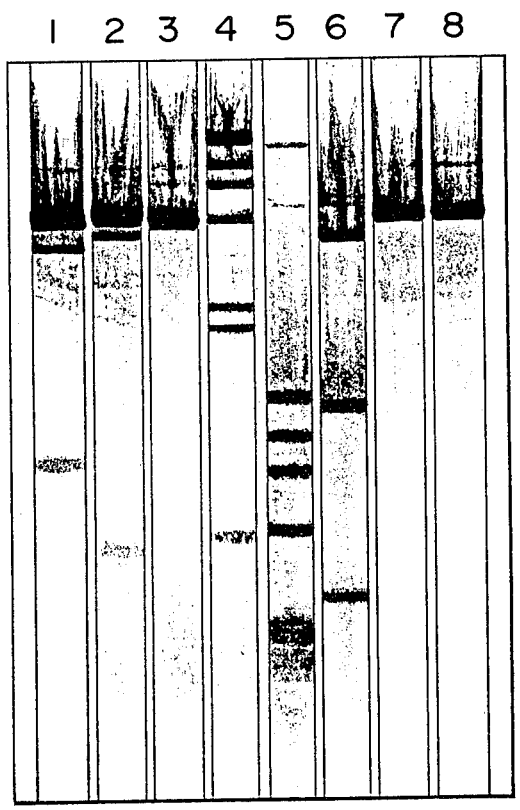
FIG. 1 is a schematic diagram showing the results of agarose gel electrophoresis of the substrate DNA (pBR 322) treated with the enzyme of the present invention.

The DNase A of the present invention and process for the production thereof will now be described in detail.

The microorganisms which may be used to obtain the DNase A of this invention belong to the genus Saccharomyces or Pichia of Saccharomycetaceae and are capable of producing the DNase A. Examples of such microorganisms include (i) *Saccharomyces uvarum* Beijerinck, (ii) *Saccharomyces cerevisiae* Hansen No. 1, and (iii) *Saccharomyces cerevisiae* Hansen No. 2 which belong to the genus Saccharomyces, and (iv) *Pichia membranaefaciens* Hansen which belongs to the genus Pichia.

The species of (i) *Saccharomyces uvarum* Beijerinck was assigned the American Type Culture Collection (12301 Parklawn Drive, Rockville, Md. 20852) (hereinafter referred to as "ATCC") ATCC accession number 9080, which is on deposit with ATCC in an unrestricted deposit permitting the full access to the culture.

On the other hand, the species of (ii) *Saccharomyces cerevisiae* Hansen No. 1, (iii) *Saccharomyces cerevisiae* Hansen No. 2 and (iv) *Pichia membranaefaciens* Hansen were deposited with the Fermentation Research Institute, Agency of Industrial Science and Technology, Ministry of International Trade and Industry, Japan, International Depositary Authority (hereinafter referred to as "FERM") under the following accession numbers, respectively, FERM BP-No. 94, FERM BP-No. 95, FERM BP-No. 96: and are on deposit with FERM in an unrestricted deposit permitting the full access to the culture.

The depositories and accession numbers of the above mentioned microorganisms are shown in Table 1.

TABLE 1

| | Microorganisms | Depository | Accession No. |
|---|---|---|---|
| (i) | Saccharomyces uvarum Beijerinck | ATCC | ATCC 9080 |
| (ii) | Saccharomyces cerevisiae Hansen No. 1 | FERM | FERM BP-94 |
| (iii) | Saccharomyces cerevisiae Hansen No. 2 | FERM | FERM BP-95 |
| (iv) | Pichia membranaefaciens Hansen | FERM | FERM BP-96 |

The applicant will maintain the deposition of ATCC 9080, FERM BP-94, FERM BP-95 and FERM BP-96 in the unrestricted form until the end of the duration of a patent granted on this application if a patent is granted on this application, and thus said microorganism strains will be available to any third party at any time until the end of the duration of the patent granted on this application.

The microorganisms may be cultured according to a conventional culture method, for example, by inoculating the above-mentioned microorganism on a liquid culture medium containing aminoacid, casein hydrolyzate, glucose, etc. and culturing it at about 25° to 35° C. for 15 to 20 hours with aeration (preculture) thereafter, transferring the culture solution to a culture medium containing the same ingredients and having 20 times the volume to culture it at 30° C. for 8 hours with aeration and agitation, centrifuging the culture solution to collect the cells. The cells are disrupted by French press to obtain a cell-free extract which is treated with Polymin P (Trademark; polyethyleneimine) to precipitate and remove the nucleic acid fraction, fractionated with ammonium sulfate, and subjected to ion exchange column chromatography using phosphocellulose or DEAE-cellulose, gel filtration or a combination of these methods to separate and collect the purified Endo-DNase A.

The DNase A thus obtained is a novel nuclease having the following physico-chemical properties.

PHYSICO-CHEMICAL PROPERTIES OF THE DNASE A (1) Activity and Substrate Specificity DNA of the plasmid pBR 322 propagated in *Escherichia coli* was selected as a substrate DNA in the enzymatic reaction and treated with various restriction enzymes and the DNase A. After the enzymatic reaction, the product was subjected to the agarose (1%) gel electrophoresis to see the size of the fragmented substrate DNA and the number of cleaved positions. The results as shown in FIG. 1 were obtained. Thus, FIG. 1 is a diagram of agarose (1%) gel electrophoresis of the substrate DNA (pBR 322) treated with the DNase A. In the drawing, the numerals 1 to 3, 7 and 8 refer to fragmentation of pBR 322 DNA treated with both the DNase A and one of the following restriction enzymes respectively, and the numerals 4 to 6 refer to fragmentation of various DNA treated with only one of the following restriction enzymes, and are shown as a marker of molecular weight. All of the restriction enzymes used are commercially available.

| No. | Substrate DNA | Restriction Enzymes | | |
|---|---|---|---|---|
| 1 | pBR 322 | + Pst I | + The DNase A |
| 2 | " | + Sal I | + The DNase A |
| 3 | " | + BamH I | + The DNase A |
| 4 | λ | + Hind III | |
| 5 | φ × 174 · RF—I | + Hae III | |
| 6 | φ × 174 · RF—I | + Hpa I | |
| 7 | pBR 322 | + EcoR I | + The DNase A |
| 8 | pBR 322 | + Hind III | + The DNase A |

Figure 2:
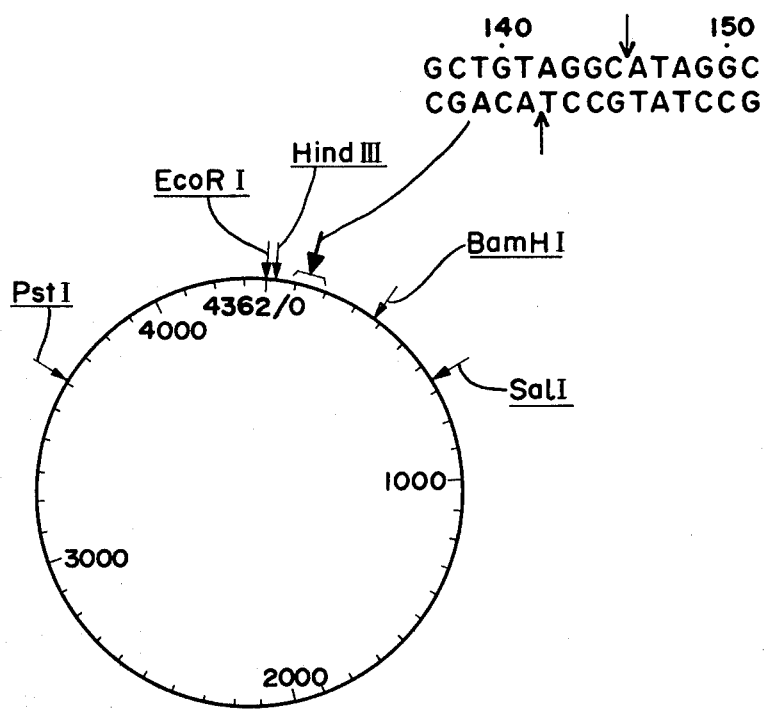
FIG. 2 is a physical map showing cleaved positions of the substrate DNA (pBR 322) treated with the enzyme of the present invention together with an enlarged view of the cleaved position of the substrate DNA.

It will be seen from FIG. 1 that the DNase A cleaves the substrate DNA (pBR 322) into fragments of specific size. FIG. 2 is a physical map which is obtained from the results shown in FIG. 1 and clearly shows the cleaved position. The cleaved position on pBR 322 DNA with a molecular weight of $2.6 \times 10^6$ daltons is shown by an arrow in FIG. 2.

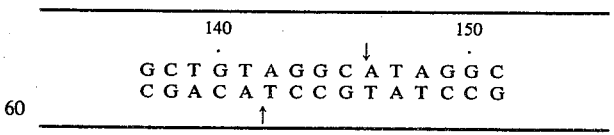

```
      140                        150
       .            ↓             .
     G C T G T A G G C A T A G G C
     C G A C A T C C G T A T C C G
                   ↑
``` note: Numbers indicate the positions on the physical map (unit; base-pairs) of pBR 322 DNA (1-4362)

From the results shown in FIGS. 1 and 2, it can be seen that the DNase A cleaves the substrate DNA at a specific site near the cleaved position on the substrate DNA (pBR 322) by treating with restriction enzyme Hind III.

Figure 3:
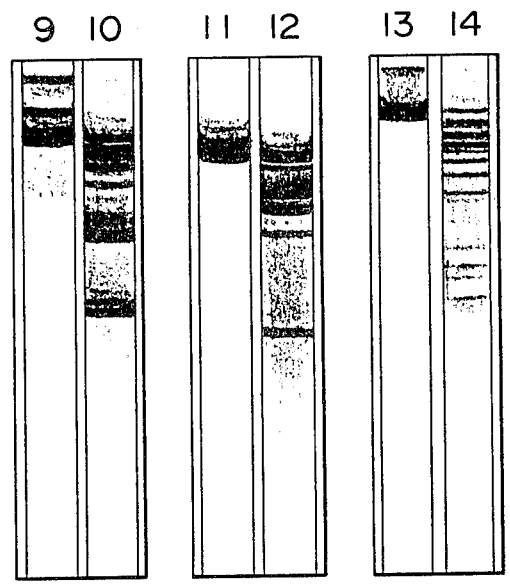
FIGS. 3 and 4 are diagrams showing fragment patterns of various substrates DNA treated with the enzyme of the present invention.
Figure 4:
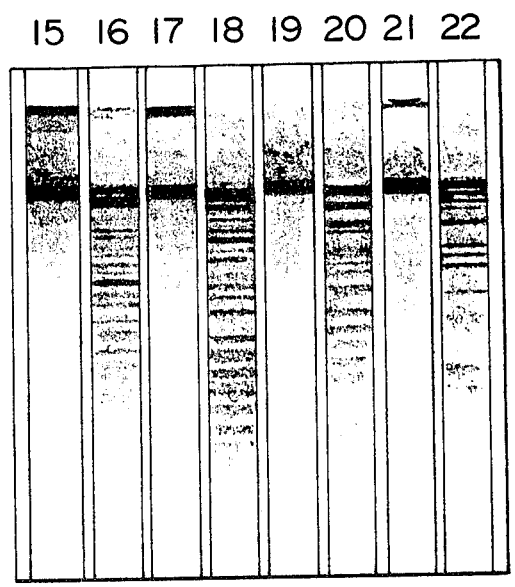

FIGS. 3 and 4 show diagrams of agarose gel electrophoresis of various substrate DNA treated with the DNase A.

FIG. 3 shows that the DNase A cleaves various substrate DNA as follows:

| No. | Substrate DNA | The DNase A | Cleaved Position |
|-----|---------------|-------------|------------------|
| 9   | φ105C phage DNA | −        | non              |
| 10  | "             | +           | several          |
| 11  | M2 phage DNA  | −           | non              |
| 12  | "             | +           | several          |
| 13  | λ phage DNA   | −           | non              |
| 14  | "             | +           | many             | note:
− ... The DNase A was not added.
+ ... The DNase A was added.

FIG. 4 shows that the DNase A cleaves various substrate DNA as follows:

| No. | Substrate DNA | The DNase A | Cleaved Position |
|-----|---------------|-------------|------------------|
| 15  | φNR2 phage DNA | −         | non              |
| 16  | "             | +           | many             |
| 17  | φ1 phage DNA  | −           | non              |
| 18  | "             | +           | many             |
| 19  | SPP1 phage DNA | −          | non              |
| 20  | "             | +           | many             |
| 21  | ρ11 phage DNA | −           | non              |
| 22  | "             | +           | many             | note:
− ... The DNase A was not added.
+ ... The DNase A was added.

From the results shown in FIGS. 3 and 4, it can be seen that the DNase A cleaves substrate DNA of φ105C phage and M2 phage at several sites, and of λ phage, φNR2 phage, φ1 phage, SPP1 phage and ρ11 phage at many sites, respectively.

The substrate DNAs used are as follows:
(1) φx174.RF—I—replicative form I DNA of *Escherichia coli* phage φx174
(2) φ105C—Bacillus phage φ105C grown on *Bacillus subtilis* Marburg 168
(3) M2—Bacillus phage M2 grown on *Bacillus subtilis* Marburg 168
(4) λ—E. coli phage λ grown on *Escherichia coli* B
(5) φ1—Bacillus phage φ1 grown on *Bacillus subtilus* Marburg 168
(6) SPP1—Bacillus phage SPP1 grown on *Bacillus subtilis* Marburg 168
(7) ρ11—Bacillus phage ρ11 grown on *Bacillus subtilis* Marburg 168

The restricted enzymes used are as follows:
(1) Pst I—separated from *Providencia staurtii* 164
(2) Sal I—separated from *Streptomyces albus* G
(3) BamH I—separated from *Bacillus amyloliquefaciens*
(4) Hind III—separated from *Haemophillus influenzae* d.
(5) Hae III—separated from *Haemophillus aegyptius*
(6) Hpa I—separated from *Haemophillus parainfluenzae*
(7) EcoR I—separated from *Escherichia coli* RY13

It has been concluded from the results shown in FIGS. 1 to 4 that the DNase A is an Endo-deoxyribonuclease which has a substrate specificity of recognizing specific base sequence in a molecule of various substrate DNA and cleaving the DNA chain at one or more of the specific positions therein to produce specific DNA fragments.

(2) Optimum pH

The optimum pH for the enzymatic activity was measured in 50 mM Tris-hydrochloric acid buffer. The activity of the DNase A was found at between pH 6.5 and pH 10.0 and was maximum at between pH 6.8 and pH 8.5.

(3) Range of Working Temperature

Between about 30° C. and about 37° C.

(4) Method for Measuring Potency

The DNase A was added to a solution containing 50 mM Tris-hydrochloric acid buffer (pH 7.5), 5 mM 2-mercaptoethanol, 50 mM KCl, 10 mM $MgCl_2$ and various bacteriophage DNA or plasmid DNA and the mixture was treated at 37° C. for 60 minutes. The reaction products were subjected to 0.7% or 1% agarose gel electrophoresis. The resulting agarose plates were exposed to ultraviolet rays in the presence of ethidium bromide. Fluorescence thus radiated was photographed to detect the electrophoretic pattern as bands on the film. The number of the bands and positions and amounts of each band were measured.

(5) Inhibition, Activation and Stabilization

The DNase A was activated by $Mg^{++}$ which may be replaced by the other bivalent metal ion, especially $Mn^{++}$. The DNase A was inhibited by more than 0.2 mole of NaCl or KCl.

(6) Method of Purification

A DNase A-producing microorganism belonging to the genus Saccharomyces or Pichia is cultured. The cell-free extract obtained from the cell is treated with Polymin P (Trademark; polyethyleneimine) to precipitate and remove the nucleic acid fraction, then it is fractionated with ammonium sulfate and is subjected to ion exchange column chromatography using phosphocellulose, DEAE-cellulose, or the like, gel filtration or a combination thereof to separate the purified DNase A.

(7) Molecular Weight

Molecular weight of the DNase A was measured by gel filtration method using Ultro gel AcA 44 and was about 80,000 daltons.

(8) Elementary Analysis

Elementary analysis of the DNase A has not been conducted yet, because it does not seem to characterize the DNase A.

As described above in detail, the DNase A is a novel Endo-deoxyribonuclease which has the substrate specificity of recognizing specific base sequence in double-stranded DNA molecules of some organisms such as *Escherichia coli* and bacteriophage and cleaving the strands at specified sites of the DNA to produce specific DNA fragments. The DNase A has such a high substrate specificity which has never been disclosed in any published literatures, and can efficiently be produced by the process of this invention.

The process of this invention will now be described with reference to the following Examples which are illustrated only for the explanation of this invention and are not intended to restrict the scope of this invention.

EXAMPLE 1

Preparation of Cell-free Extract

The above-mentioned *Saccharomyces cerevisiae* Hansen No. 1 (FERM BP-94) was precultured in 500 ml of a liquid medium containing 2% glucose, 2% polypeptone and 1% yeast extract, at 30° C. overnight with aeration. The pre-culture solution was inoculated to 10 l of the same culture medium as described above and cultured at 30° C. for 8 hours with aeration and agitation. The resulting culture solution was centrifuged at 10,000 rpm for 20 minutes, washed twice with distilled water to give about 200 g of the cells (18 to 20 g/1 l of culture medium) which can be freezed and stored at $-80°$ C.

The cells (200 g) were suspended in 50 ml of the buffer A (50 mM Tris-HCl buffer (pH 7.5), 1 mM EDTA, 10 mM 2-mercaptoethanol and 10% glycerol) containing 0.3 M ammonium sulfate and disrupted with French press (1,800 kg/cm$^2$). The disrupted mass was suspended in 200 ml of the buffer A containing 0.3 M ammonium sulfate. The suspension was agitated at 0° C. for 30 minutes and centrifuged at 13,000 rpm for 60 minutes at 2° C. to obtain 350 ml of the supernatant fraction I which had the activity of the DNase A.

Purification

To the fraction I thus obtained, Polymin P solution (10%, pH 8.0) was added to get 0.4% of the final concentration with agitation and the mixture was agitated at 0° C. for 40 minutes. Then, the mixture was centrifuged at 13,000 rpm for 30 minutes at 2° C. to obtain a supernatant to which crushed ammonium sulfate was added to get a 70% saturated solution which was then agitated at 0° C. for 50 minutes and was further centrifuged at 16,000 rpm for 30 minutes at 2° C. to give a precipitate. The precipitate was dissolved in 100 ml of the buffer B (containing 20 mM phosphate buffer (pH 6.8), 1 mM EDTA, 10 mM 2-mercaptoethanol and 10% glycerol). The resulting solution was dialyzed with 4 l of the buffer B containing 0.15 M KCl for 4 hours to obtain 154 ml of the fraction II.

The fraction II was adsorbed on a phosphocellulose column ($\phi$3.2×23 cm) previously conditioned with the buffer B containing 0.15 M KCl. By eluting with the buffer B, the active fraction was eluted to give 230 ml of the fraction III.

The resulting fraction III was diluted to double volume with the buffer B, which was adsorbed on a phosphocellulose column ($\phi$3.2×25 cm) which was then washed with 400 ml of the buffer B, afterwhich eluted with 0 to 0.8 M linear concentration gradient of KCl. The active fraction was eluted with about 0.3 M KCl, 166 ml of the fraction IV was obtained.

Ammonium sulfate was added to the fraction IV to get a 70% saturated solution which was then agitated at 0° C. for 30 minutes and centrifuged at 27,000 rpm for 20 minutes at 2° C. The resulting sediment was dissolved in 6 ml of the buffer A, then adsorbed on a column packed with Toyopearl HW 65F ($\phi$1.9×45 cm) previously conditioned with the buffer A containing 1 M KCl and eluted with the buffer A.

The active fractions collected were dialyzed with 2 l of the buffer A containing 50% glycerol for 4 hours, 6 ml of the fraction V containing the DNase A was obtained.

The DNase A thus obtained can be stored at $-20°$ C.

EXAMPLE 2

The procedure of Example 1 except that *Saccharomyces cerevisiae* Hansen No. 2 (FERM BP-95) was used instead of *Saccharomyces cerevisiae* Hansen No. 1 was repeated. 5 Ml of the fraction V of the DNase A was obtained.

EXAMPLE 3

The procedure of Example 1 except that *Saccharomyces uvarum* Beijerinck (ATCC 9080) was used instead of *Saccharomyces cerevisiae* Hansen No. 1 was repeated. 6 Ml of the fraction V of the DNase A was obtained.

EXAMPLE 4

Preparation of Cell-free Extract

The above-mentioned *Pichia membranafacience* Hansen (FERM BP-96) was precultured in 500 ml of a liquid medium containing 2% glucose, 2% polypeptone and 1% yeast extract, at 30° C. overnight with aeration. The pre-culture solution was inoculated to 10 l of the same culture medium as described above and cultured at 30° C. for 16 hours with aeration and agitation. The resulting culture solution was centrifuged at 10,000 rpm for 20 minutes, washed twice with distilled water to give about 240 g of the cells (20 to 23 g/1 l of culture medium) which can be freezed and stored at $-80°$ C.

The cells (240 g) were suspended in 50 ml of the buffer A (50 mM Tris-HCl buffer (pH 7.5), 1 mM EDTA, 10 mM 2-mercaptoethanol and 10% glycerol) containing 0.3 M ammonium sulfate and disrupted with French press (1,800 kg/cm$^2$). The disrupted mass was suspended in 200 ml of the buffer A containing 0.3 M ammonium sulfate. The suspension was agitated at 0° C. for 30 minutes and centrifuged at 13,000 rpm for 60 minutes at 2° C. to obtain 300 ml of the supernatant fraction I which had the activity of the DNase A.

Purification

To the fraction I thus obtained, Polymin P solution (10%, pH 8.0) was added to get 0.4% of the final concentration with agitation and the mixture was agitated at 0° C. for 40 minutes. Then, the mixture was centrifuged at 13,000 rpm for 30 minutes at 2° C. to obtain a supernatant to which crushed ammonium sulfate was added to get a 70% saturated solution which was then agitated at 0° C. for 50 minutes and was further centrifuged at 16,000 rpm for 30 minutes at 2° C. to give a precipitate. The precipitate was dissolved in 100 ml of the buffer B (containing 20 mM phosphate buffer (pH 6.8), 1 mM EDTA, 10 mM 2-mercaptoethanol and 10% glycerol). The resulting solution was dialyzed with 4 l of the buffer B containing 0.15 M KCl for 4 hours to obtain 140 ml of the fraction II.

The resulting fraction II was diluted to double volume with the buffer B, which was adsorbed on a phosphocellulose column ($\phi$3.2×40 cm) which was then washed with 500 ml of the buffer B, afterwhich eluted with 0 to 0.8 M linear concentration gradient of KCl. The active fraction was eluted with 0.3 to 0.4 M KCl, 200 ml of the fraction III was obtained.

Ammonium sulfate was added to the fraction III to get a 70% saturated solution, which was then agitated at 0° C. for 30 minutes and centrifuged at 27,000 rpm for 20 minutes at 2° C. The resulting sediment was dissolved in 6 ml of the buffer A, then adsorbed on a column packed with Toyopearl HW 65F ($\phi$2.6×43 cm)

previously conditioned with the buffer A containing 1 M KCl and eluted with the buffer A.

The active fractions collected were dialyzed with 2 l of the buffer A containing 50% glycerol for 4 hours, 6 ml of the fraction IV containing the DNase A was obtained.

The DNase A thus obtained can be stored at −20° C.

What we claim is:

1. Endo-deoxyribonuclease A (Endo-DNase A) which has the substrate specificity of recognizing specific base sequence in double-stranded deoxyribonucleic acid (DNA) molecules and cleaving the strands at specified site(s) in the DNA to produce specific DNA fragments: the DNase A being capable of recognizing the following nucleotide sequence in the molecule of pBR 322 DNA and cleaving the said DNA in one position sequence at the indicated vertical arrows,

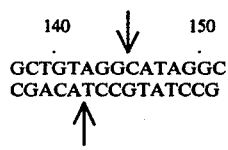

and cleaving φ105C phage DNA and M2 phage DNA in several positions, and λ phage DNA, φNR2 phage DNA, φ1 phage DNA, SPP1 phage DNA and ρ11 phage DNA in many positions; having the optimum pH of 6.5 to 10.0 in 50 mM Tris-HCL buffer; having the working temperature of about 30° to about 37° C.; being activated with $Mg^{++}$ or $Mn^{++}$; being inhibited with more than 0.2 M of NaCl or KCl, and having molecular weight of about 80,000 daltons measured by a gel filtration method using Ultro gel AcA 44, said enzyme being obtained from a cell-free extract of a DNaseA-producing microorganism belonging to the genus Saccharomyces or Pichia in a culture medium, collecting the cells thereof, obtaining cell-free extract therefrom, separating and collecting the DNase A.

2. A process for the production of the Endo-DNase A as defined claim 1 which comprises culturing a DNase A-producing microorganism belonging to the genus Saccharomyces, collecting the cells, obtaining cell-free extract therefrom, and separating and collecting the DNase A from the cell-free extract.

3. The process of claim 2 in which the cell-free extract is treated to remove nucleic acid fraction therefrom, and at least one method selected from ammonium sulfate fractionation, ion exchange chromatography and gel filtration is used to separate and collect the DNase A.

4. A process for the production of the Endo-DNase A as defined claim 1 which comprises culturing a DNase A-producing microorganism belonging to the genus Pichia, collecting the cells, obtaining cell-free extract therefrom, and separating and collecting the DNase A from the cell-free extract.

5. The process of claim 4 in which the cell-free extract is treated to remove nucleic acid fraction therefrom, and at least one method selected from ammonium sulfate fractionation, ion exchange chromatography and gel filtration is used to separate and collect the DNase A.